(12) United States Patent
Cramers et al.

(10) Patent No.: US 7,312,364 B2
(45) Date of Patent: Dec. 25, 2007

(54) EQUILIBRIUM REACTION AND GAS/LIQUID REACTION IN A LOOP REACTOR

(75) Inventors: Peter Cramers, Liestal (CH); Gerhard Kettenbach, Grenzach-Wyhlen (DE); Andreas Sellmann, Ratingen (DE); Volker Zellmer, Bottrop (DE)

(73) Assignee: Goldschmidt GmbH (DE)

( * ) Notice: Subject to any disclaimer, the term of this patent is extended or adjusted under 35 U.S.C. 154(b) by 162 days.

(21) Appl. No.: 11/327,599

(22) Filed: Jan. 6, 2006

(65) Prior Publication Data

US 2006/0155152 A1    Jul. 13, 2006

(30) Foreign Application Priority Data

Jan. 8, 2005    (DE) .................. 10 2005 001 076

(51) Int. Cl.
*C07C 41/03* (2006.01)
(52) U.S. Cl. .................... 568/679; 568/618
(58) Field of Classification Search .............. None
See application file for complete search history.

(56) References Cited

U.S. PATENT DOCUMENTS 6,342,199 B1 *   1/2002   Ellis .................. 423/659

FOREIGN PATENT DOCUMENTS

EP           0 419 419 A1     3/1991
WO           WO 98/17381       4/1998

\* cited by examiner

*Primary Examiner*—Rosalynd Keys
(74) *Attorney, Agent, or Firm*—Frommer Lawrence & Haug LLP

(57) ABSTRACT

The invention relates to a process for simultaneously performing two chemically successive reactions in a loop reactor, specifically reaction I) an optionally catalyzed equilibrium reaction between high-boiling liquid reactants, in which essentially one high boiler is formed as an intermediate and at least one low boiler as a by-product, and reaction II) a substantially diffusion-controlled reaction in which the liquid intermediate is reacted with at least one gaseous reactant to give the end product, wherein reactions (I) and (II), optionally after a start phase, are allowed to proceed simultaneously in the same apparatus, specifically loop reactor, and the loop reactor has a connectable gas-liquid circulation system coupled via an ejector mixing nozzle, in which circulated liquid phase is mixed in the ejector mixing nozzle with newly supplied gaseous reactant of reaction (II) (6) and/or gaseous reactant of reaction (II) aspirated by means of the ejector from the reactor via a connectable condenser (5), and fed to the reactor by a liquid jet ejector (2) for the reaction, the low-boiling by-product(s) of reaction (I) and also any low-boiling solvent being condensed and discharged in the condenser continuously over the duration of the process. In particular, the invention relates to a process for etherifying high-boiling polyether alcohols.

11 Claims, 3 Drawing Sheets

EQUILIBRIUM REACTION AND GAS/LIQUID REACTION IN A LOOP REACTOR

The invention relates to a process for simultaneously performing two chemically successive reactions in a loop reactor which has a liquid jet ejector and also a closed condensation system. In particular, the invention relates to a process for etherifying high-boiling polyether alcohols.

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention.

Chemical production processes which comprise two or more chemically successive reactions, i.e. reactions which build on one another, in which one reaction consists in an equilibrium reaction, for example between high-boiling liquid reactants, and the reaction which builds thereon is a substantially diffusion-controlled reaction, in which the liquid intermediate of the first reaction is reacted with at least one gaseous reactant to give the end product, are currently carried out on the industrial scale in a manner which separates the two reactions spatially, temporally and/or in terms of process technology.

For example, in an industrial scale alkylation of polyether alcohols by the Williamson method, in a first step (scheme 1), sodium polyether alkoxide and methanol are initially prepared from polyether alcohol (PEOH) and sodium methylate.

  (Scheme 1)

PEOH + CH$_3$ONa $\rightleftharpoons$ PEONa + CH$_3$OH

The reaction equilibrium of this equilibrium reaction lies strongly to the side of the reactants and it therefore has to be shifted to the product side by effectively distilling off the methanol which forms. However, this does not succeed completely, since there is a restriction in the maximum temperature to temperatures below 130° C. owing to thermally induced rearrangement reactions and for process technology reasons in the vacuum to be employed. A vacuum of less than 20 mbar can only be realized industrially with disproportionately high costs. In addition, the equilibrium reaction entails a high excess of sodium methylate. Sodium methylate can in principle be used in the form of a methanolic solution or else in powder form. When methanolic solution is used, the methanol solvent, just like the methanol formed in the reaction, has to be removed with maximum efficiency in order to shift the reaction equilibrium to the product side. High-performance and costly distillation processes, such as the use of thin-film evaporators, are ruled out at the amounts of methanol which occur here. Sodium methylate is therefore in many cases added in powder form, which, however, requires the hazardous handling of highly hygroscopic, self-igniting, corrosive powder.

In a second step, sodium polyether alkoxide which still comprises reactants, especially an excess of sodium methylate, is reacted in a gas-liquid reactor with gaseous methyl chloride (scheme 2).

  (Scheme 2)

PEONa + CH$_3$Cl $\longrightarrow$ PEOCH$_3$ + NaCl

Excess sodium methylate reacts in an undesired side reaction to give dimethyl ether which has to be disposed of as offgas. Methyl chloride (MeCl) reacts in an amount equimolar to the sodium methylate used, i.e. a high excess of sodium methylate means a high demand for methyl chloride (scheme 3).

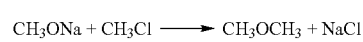  (Scheme 3)

CH$_3$ONa + CH$_3$Cl $\longrightarrow$ CH$_3$OCH$_3$ + NaCl

A special case of a state of the art process is illustrated by alkoxide formation according to scheme 1, in which sodium hydroxide solution, NaOH, is used instead of sodium methylate.

It is known that the yield of the described and comparable reactions can be increased by a series of methylation stages in a plurality of reactors, each methylation stage being followed by a distillation step in which methanol is removed at 120° C. down to a pressure of 20 mbar. However, the cost and complexity of the apparatus and process technology is considerable.

The state of the art also discloses loop reactors, for which it is possible, as described, for example in EP-A-0 419 419, for a gas circulation system and a liquid circulation system to be arranged around the reactor and each be coupled via an ejector mixing nozzle (liquid jet ejector) working by the Venturi principle. Ejector mixing nozzles generate large phase exchange surfaces between reaction gas and liquid, in which case the reaction gas supplied in gaseous form is inevitably mixed constantly and intensively, and circulated, with the inert gas which may be present. Such reactors are used especially for the performance of gas-liquid reactions which feature a very high reaction rate and are therefore determined only by the mass transfer from the gas phase into the liquid phase, i.e. whose kinetics are diffusion-controlled; see, for example WO-A-98/17381.

It is also known that equilibrium reactions of high-boiling substances in which a low boiler is formed, for example esterification reactions in the field of fat chemistry, can be allowed to proceed in the above-described loop reactors with closed gas circulation systems. Such reactions are, for example:

R—COOH (fatty acid) +

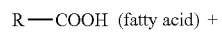 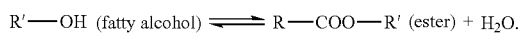

R'—OH (fatty alcohol) $\rightleftharpoons$ R—COO—R' (ester) + H$_2$O.

The fatty acid and fatty alcohol reactants and the ester which forms are high-boiling liquids. The water forms in vaporous form under the process conditions, and is sucked out of the gas space of the reactor with the aid of the ejector via a condenser and condensed out continuously in order to shift the reaction equilibrium to the desired side.

Against this background, it is an object of the invention to develop a process for performing two chemically successive reactions in a loop reactor, comprising (reaction I) an optionally catalyzed equilibrium reaction of at least two high-boiling liquid reactants, in which essentially one high boiler is formed as an intermediate and at least one low boiler as a by-product, and (reaction II) a substantially diffusion-controlled reaction in which the liquid intermediate from reaction I is reacted with at least one gaseous reactant to give the end product, which overcomes the disadvantages and problems outlined. In particular, there is the need to provide a corresponding process for etherifying high-boiling polyether alcohols.

In batchwise operation, the process is intended to lead to a capacity increase per plant by shortening the batch cycle time, and to reduce the specific raw material requirement. In addition, further objects of the invention are simpler apparatus, safer handling of the reactants and the integration of an economically viable and ecologically optimal offgas treatment of the gaseous by-products.

Figure 1:
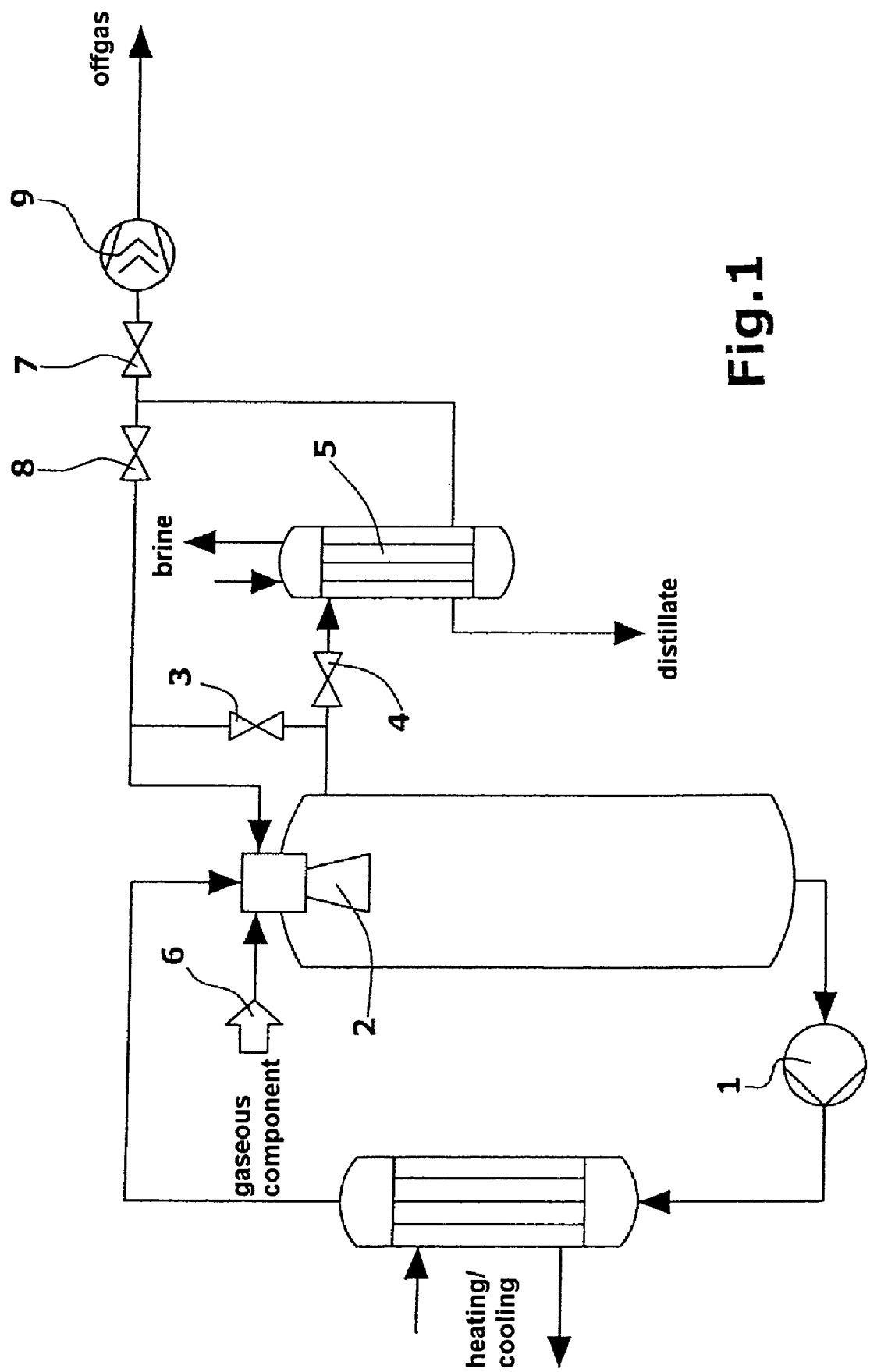
FIG. 1 depicts a loop reactor of the invention.

The object of the invention is achieved by a process for performing two chemically successive reactions in a loop reactor, specifically (reaction I) an optionally catalyzed equilibrium reaction of at least two high-boiling liquid reactants, in which essentially one high boiler is formed as an intermediate and at least one low boiler as a by-product, and (reaction II) a substantially diffusion-controlled reaction in which the liquid intermediate from reaction I is reacted with at least one gaseous reactant to give the end product, wherein reactions I and II, optionally after a start phase, are allowed to proceed simultaneously in the same apparatus specifically a loop reactor, and the loop reactor has a connectable gas-liquid circulation system coupled via an ejector mixing nozzle, in which circulated liquid phase is mixed in the ejector mixing nozzle with newly supplied gaseous reactant of reaction II 6 and/or gaseous reactant of reaction II aspirated by means of the ejector from the reactor via a connectable condenser 5, and fed to the reactor by a liquid jet ejector 2 for the reaction, the low-boiling by-product(s) of reaction I and also any low-boiling solvent being condensed and discharged in the condenser 5 continuously over the duration of the process.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Although the configuration of a particularly preferred embodiment will be described in detail below, it should be emphasized here particularly that the process according to the invention is also suitable especially for those processes of the general definition of the main claim which are not restricted to the etherification of high-boiling, liquid alkyl-or alkenyl-started polyether alcohols of the general formula (1)

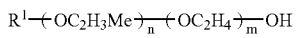

where
$R^1$ is an alkyl- or alkenyl radical having 1 to 5 carbon atoms,
Me is a methyl radical,
n and m are each an integer in the range from 0 to 90 and the sum of n+m is in the range from 5 to 90.

In the first reaction, an equilibrium reaction of high-boiling reactants accordingly forms a high boiler as an intermediate and at least one low boiler as a by-product which is condensed out in the closed gas circulation system continuously to shift the reaction equilibrium. In the second reaction, the high-boiling intermediate which forms is then reacted with a gaseous reactant with utilization of the above-described advantages of the particularly suitable loop reactor for a gas-liquid reaction to give the desired end product, the condensation gas circuit remaining connected. Since the conversion in the second reaction changes the mixture composition, the first equilibrium reaction also proceeds further, and, during the second reaction, the low-boiling by-product of the first reaction is also formed. By virtue of the low boiler of the first reaction still being distilled off continuously during the second reaction, the equilibrium is shifted further in the desired direction and very high conversions are achieved.

An example of the process according to the invention is the nitrilation of fatty acid with subsequent hydrogenation to the amine:

(Scheme 4)

(Scheme 5)

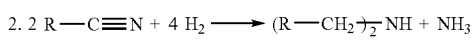

In the process according to the invention, both reactions can be performed immediately successively in the same loop reactor. In this way, the water formed in reaction I can still be removed from the mixture in the course of the condensation of the $NH_3$ in reaction II, in order thus to increase the overall conversion.

An appropriately suitable loop reactor which has a connectable gas-liquid circulation system coupled via an ejector mixing nozzle is known per se in the prior art and is used, for example, for the quaternization of amines with methyl chloride. However, the simultaneous performance of a rapid gas-liquid reaction with a superimposed equilibrium reaction while continuously distilling off a low-boiling by-product is to date not known in the prior art.

FIG. 1 shows such a loop reactor. The reactor has a reactor and a circulation system which is operated with a circulation pump 1 via a heat exchanger. The circulated liquid is mixed in the loop reactor shown with aspirated, gaseous reactant 6 in an ejector mixing nozzle 2, and conveyed back into the reactor. In addition, there is a connection, closable with a valve 3, for the gas space of the reactor with the aspiration orifice of the ejector mixing nozzle 2, through which the gas phase can be aspirated, mixed with gaseous reactant 6 and circulated liquid phase and conveyed back into the reactor. A closed gas circulation system with a cooler/heat exchanger 5 and one withdrawal point each for distillate and offgas can be connected via a valve 4 to this connection. In this case, the heat exchanger 5 can be operated as a condenser 5 by cooling the aspirated gas below the boiling point. Control of the condensation temperature allows determination of the composition in which the gas constituents condense out. Other parts of the loop reactor include valve 7, valve 8 and vacuum unit 9.

For the reaction of gases with liquids, such loop reactors have advantages with regard to operational safety and product quality, since local inhomogeneities with regard to concentrations and temperature can be prevented efficiently.

High boilers and low boilers in the context of the present invention mean two liquids whose boiling points are so far apart that a thermal process can be employed to separate the two substances. High boilers and low boilers can be determined by those of skill in the art from standard references in the art, e.g. *Vogel's Textbook of Practical Organic Chemistry* (*Fifth Edition*), eds. Furniss et al., Longman Science & Technical, (1989)).

An example of a high boiler is a liquid which, under standard conditions of temperature and pressure, has a boiling point of at least 200° C. Examples of high boilers include but are not limited to dodecane, octadecane, pentylcyclohexane, dodecene, cyclohexylbenzene, naphthalene, anthracene, benzyl alcohol, polyether alcohols and mixtures thereof.

The polyether alcohol containing one or more functional hydroxyl groups and is typically an adduct of an aliphatic, cycloaliphatic, or aromatic polyhydroxy compound such as an adduct of an alkylene oxide and a polyhydric alcohol or polyhydric alcohol ether, a hydroxyl-terminated prepolymer of such adduct and an organic polyisocyanate, or a mixture of such adducts with such prepolymers. In one embodiment of the invention, the polyether alcohol may contain just one hydroxyl group such as an alkyl polyethylene glycol, an alkylaryl polyethylene glycol, or a polycyclic alkyl polyethylene glycol where the alkyl group contains 1 to 20 carbon atoms.

In another embodiment of the invention, the high boiler has a boiling point of at least 300° C.

Accordingly, low boilers are preferably liquids which, under standard conditions of temperature and pressure, have a boiling point of up to 150° C. Examples of low boilers include but are not limited to methanol, ethanol, propanol, butanol, pentanol, pentane, hexane, heptane, octane, benzene, toluene, ethylbenzene, xylene and mixtures thereof.

In another embodiment of the invention, the low boiler has a boiling point of up to 100° C.

The combination of the two reactions in the process according to the invention allows an overall conversion higher by approx. 5 to 10% to be achieved, so that, in the preparation of alkylated polyether alcohols, the excess of sodium methylate and hence also of methyl chloride and the formation of dimethyl ether as a by-product from the reaction of the sodium methylate excess with methyl chloride can be reduced in the same order of magnitude.

According to the invention, the ejector mixing nozzle (2) is a mixing nozzle working by the Venturi principle.

The process according to the invention can advantageously be carried out continuously and preferably batchwise. In batchwise mode, the process additionally has the advantage that, in comparison to continuous thermal separating processes, in which the desired end content has to be attained in one process stage (for example thin-film evaporator unit), no additional flashbox (batch vessel with circulation heat exchanger or evaporator) is needed, which would otherwise be unavoidable for the reduction of the apparatus costs owing to the large amount of solvent in the feed. In addition, it is not necessary in this way to implement any continuous step into a batch process chain. In the process according to the invention, merely small product residues remain in the reactor in the event of a product change. The advantage of batchwise operation, the possibility of preparing different products in one plant, is thus promoted.

The process according to the invention can advantageously be performed in such a way that a start phase is provided in which the high-boiling liquid reactants and optionally one or more catalysts are initially charged, the high-boiling liquid reactants optionally being present in a low-boiling solvent, and reaction I is carried out with condensation and discharge of the volatile by-product(s) and any solvent, either in a closed condensation gas circuit or by aspirating the inert gases by means of a vacuum unit via a condenser, until the distillation parameters predefined according to the process and plant technology have been attained.

In this case, the process parameters for distillation of the volatile by-product(s) by so-called stripping with nitrogen can be improved considerably in the process according to the invention. To this end, after attainment of the end vacuum limited by the vacuum unit 9 (see FIG. 1) and the distillation temperature limited for product quality reasons, nitrogen is added (feedpoint 6) via the ejector. First, a partial pressure reduction of the volatile by-product(s) distills it/them off further. The principle of stripping with nitrogen can also be explained as follows: the fine distribution of the gaseous nitrogen in the liquid phase, which is achieved by a Venturi nozzle, increases the phase interface or the gas/liquid exchange surface to an extreme extent. The distillation is accelerated by the large mass transfer surface.

It may be advantageous in the preparation of alkylated polyether alcohols to carry out a start phase in which initially only the equilibrium reaction (reaction I) proceeds up to a high conversion, since direct addition of methyl chloride, in a side reaction to reaction II, reduces the sodium methylate excess needed for the equilibrium reaction I by the reaction with methyl chloride to give dimethyl ether.

However, the invention also envisages initially charging the high-boiling liquid reactants and optionally one or more catalysts, the high boiling liquid reactants optionally being present in a low-boiling solvent, and reactions (I) and (II) being carried out substantially without a start phase. In other words, it is possible in this case for both reactions, specifically reaction (I) and reaction (II), to proceed simultaneously and successively from the start onward. In this way, the reaction is simpler and can attain an even higher degree of automation.

A further aspect of the optimal process design is the offgas treatment. In the process according to the invention, an offgas incineration is advantageously additionally carried out, in which case the by-product from reaction (I) may function as a carrier fuel. This has the advantage over offgas purification by low-temperature condensation that the associated disadvantages of discontinuous occurrence of condensate, and also of costly and inconvenient disposal of the condensate, for example pressure-liquefied gases such as dimethyl ether or methyl chloride, are avoided. Compared to conventional scrubber systems, the process according to the invention offers the advantage that the disadvantage of different absorption behavior of the different offgas constituents, varying offgas loadings and the occurrence of wastewater, can be avoided.

A particularly advantageous embodiment of the process according to the invention for etherifying high-boiling, liquid alkyl- or alkenyl-started polyether alcohols of the general formula (1)

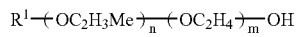

where

R$^1$ is an alkyl- or alkenyl radical having 1 to 5 carbon atoms,
Me is a methyl radical,
n and m are each an integer in the range from 0 to 90 and the sum of n+m is in the range from 5 to 90,
in a loop reactor, comprising, as reaction (I) a deprotonation of the polyether alcohol, with a high-boiling, liquid alkali metal methylate, ethoxide or propoxide, optionally in the presence of a low-boiling solvent to form substantially a high-boiling alkali metal polyether alkoxide intermediate and at least one low-boiling alcohol as a by-product and, as reaction (II),
an ether coupling in which the liquid alkali metal polyether alkoxide intermediate is reacted with gaseous alkyl halide to give the end product,
therefore envisages that reactions (I) and (II), optionally after a start phase, are allowed to proceed simultaneously and the loop reactor has a gas-liquid circulation system coupled via an ejector mixing nozzle, in which circulated liquid phase is mixed in the ejector mixing nozzle with newly supplied gaseous alkyl halide of reaction (II) (6) and/or alkyl halide of reaction (II) aspirated by means of the ejector from the reactor via a condenser (5), and fed to the reactor by a liquid jet ejector (2) for the reaction, the low-boiling alcohol(s) of reaction (I) and also any low-boiling solvent being condensed and discharged in the condenser continuously over the duration of the process.

Specifically, the process according to the invention can be configured by providing a start phase in which the high-boiling liquid polyether alcohol is initially charged, alkali metal methylate, ethylate or propylate, optionally dissolved in low-boiling solvent, especially methanol, ethanol or propanol, is added, and reaction (I) is carried out with condensation and discharge of the volatile alcohol(s) and any solvent, either in a closed condensation gas circuit or by aspirating the inert gases by means of a vacuum unit via a condenser, until the distillation parameters predefined according to the process and plant technology have been attained, for example up to a conversion of from 90 to about 100 mol % based on the polyether alcohol. To increase the efficiency of the distillation, it is possible to carry out the above-described nitrogen stripping at the end of the distillation. In another embodiment of the invention the conversion is from 90 to 95 mol % based on the polyether alcohol.

For example, the hazardous handling of sodium methylate powder is avoided by the use of 30% methanolic sodium methylate solution. Moreover, the methanol solvent used can serve as a carrier fuel in the offgas incineration plant.

The reduction of the sodium methylate excess by up to 60% compared to the prior art allows the necessary raw material use and thus also the formation of the dimethyl ether in the process according to the invention to be reduced.

Ideal conversions had been achieved when the reaction was carried out down to a residual alkali number of less than 0.1 mg KOH/g. The residual alkali number is a measure of the reaction of sodium ions of the polyether alkoxide or alkali metal alkoxide with methyl chloride, i.e. only for the conversion of reaction II. It is determined by titration with 0.1 N HCl against phenolphthalein as the indicator and is generally converted to mg KOH/g (alkali number). In the event of full conversion of alkoxide groups, the alkali number would be 0 mg KOH/g. What is crucial for the overall conversion over both reactions is the residue of polyether alcohol. Since the determination of the residual OH number is analytically complex, the following is always based on the residual alkali number.

The invention will now be further described by way of the following non-limiting examples.

EXAMPLES

Example 1

An apparatus according to FIG. 1 with a loop reactor of capacity 50 l in the reactor was initially charged with 40 kg of a high-boiling polyether alcohol. The polyether alcohol used was an alkenyl-started polyether in the form

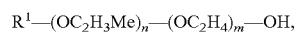

where

R$^1$ is an alkenyl radical having 3 carbon atoms and
n is 13 and
m is 4.

15 kg of 30% sodium methylate solution in methanol were then metered into the polyether alcohol in the reactor. In the closed condensation circuit with closed valve 3 and opened valve 4, the reactants were reacted at 110° according to the equilibrium reaction I, in the course of which methanol was condensed out in the condenser 5 to the extent that the condensation temperature of −15° C. allowed (start phase). According to the condensation temperature a partial methanol pressure in the gas phase and, via the phase equilibrium, a residual methanol content in the liquid phase were established, which corresponded to a conversion of the equilibrium reaction I to an extent of from 90 to 95 mol %. Once no further distillate occurred in the condenser 5 by means of this procedure, valve 8 was closed and valve 7 opened, and an end vacuum of less than 20 mbar was attained by means of vacuum unit 9. In order to even further improve the distillation conditions for methanol, nitrogen was added for about 15 min via the ejector 2 during the vacuum distillation, and the partial methanol pressure in the gas phase was thus reduced further.

Afterward, the alkoxide with methyl chloride was mixed intimately with the circulated liquid phase by means of the ejector mixing nozzle 2, and conveyed back into the reactor. The temperature in the reactor was from 110 to 130° C. In the course of this, the Williamson ether synthesis to the desired end product PEOCH$_3$ and sodium chloride proceeded according to reaction scheme 2. The end point of the reaction was determined by the attainment of a plateau in the alkali number.

Figure 3:
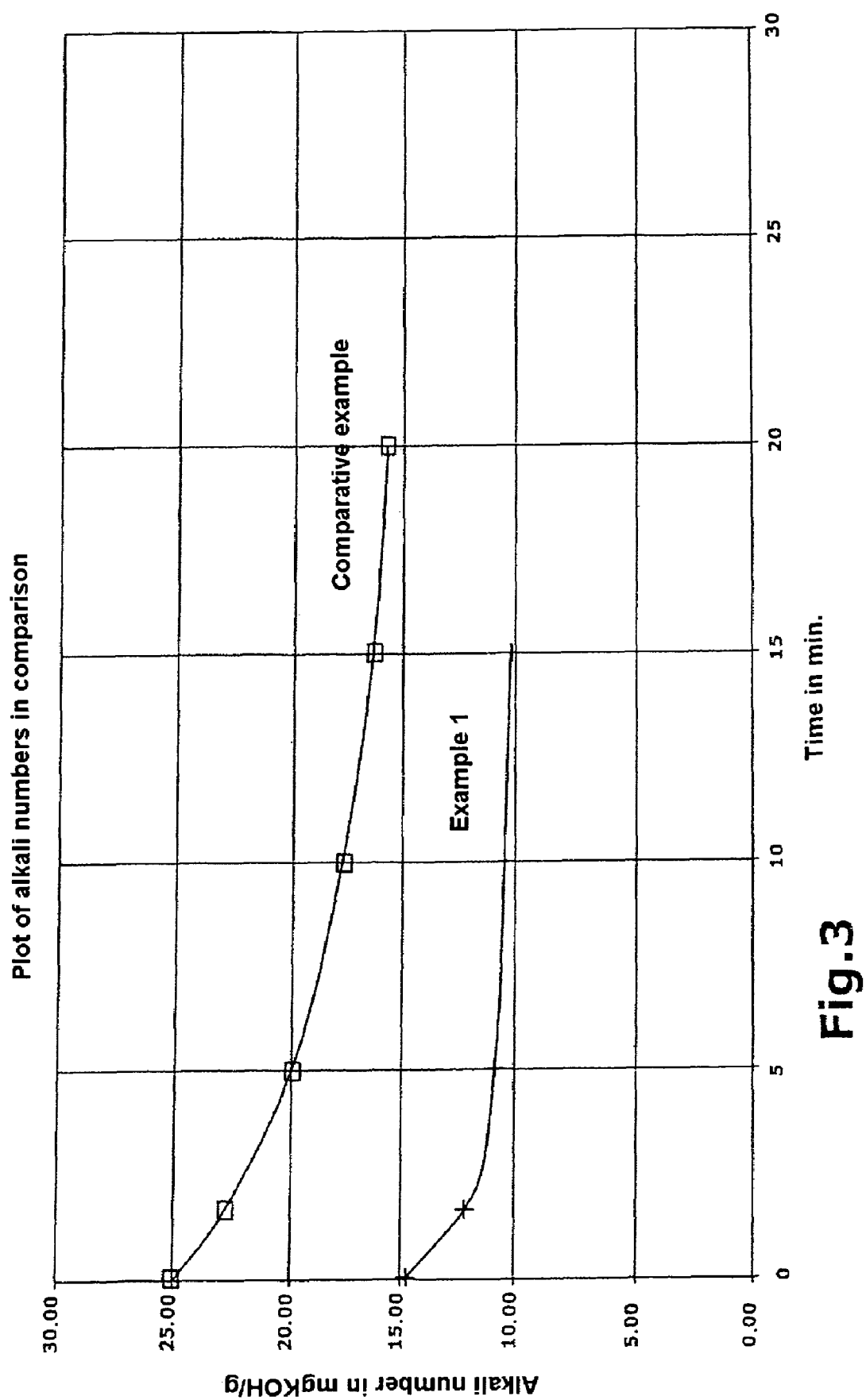
FIG. 3 depicts a plot of alkali numbers for an embodiment of the invention vs. a comparative example.

The sodium chloride remained initially in finely divided form in the product which was transferred into a stirred vessel, homogenized for neutralization with phosphoric acid and filtered through a frame filter press. The process achieved an alkali number of about 10 mg KOH/g after 15 min (FIG. 3).

COMPARATIVE EXAMPLE

The process was carried out analogously to Example 1 with the difference that, during the methylation reaction, i.e. after the start phase, the condenser in the closed gas circulation system was bypassed by closing valve 4 and opening valve 3. The end point of the reaction was determined by the attainment of a plateau in the alkali number. An alkali number of about 16 mg KOH/g was achieved after 20 min (FIG. 3).

The inventive procedure employed in Example 1 achieved overall conversions of polyether alcohol (PEOH) to the methylated polyether (PE-OCH$_3$) of from 90 to about 100%. Degrees of methylation customary in the prior art are from about 80 to 90%.

Figure 2:
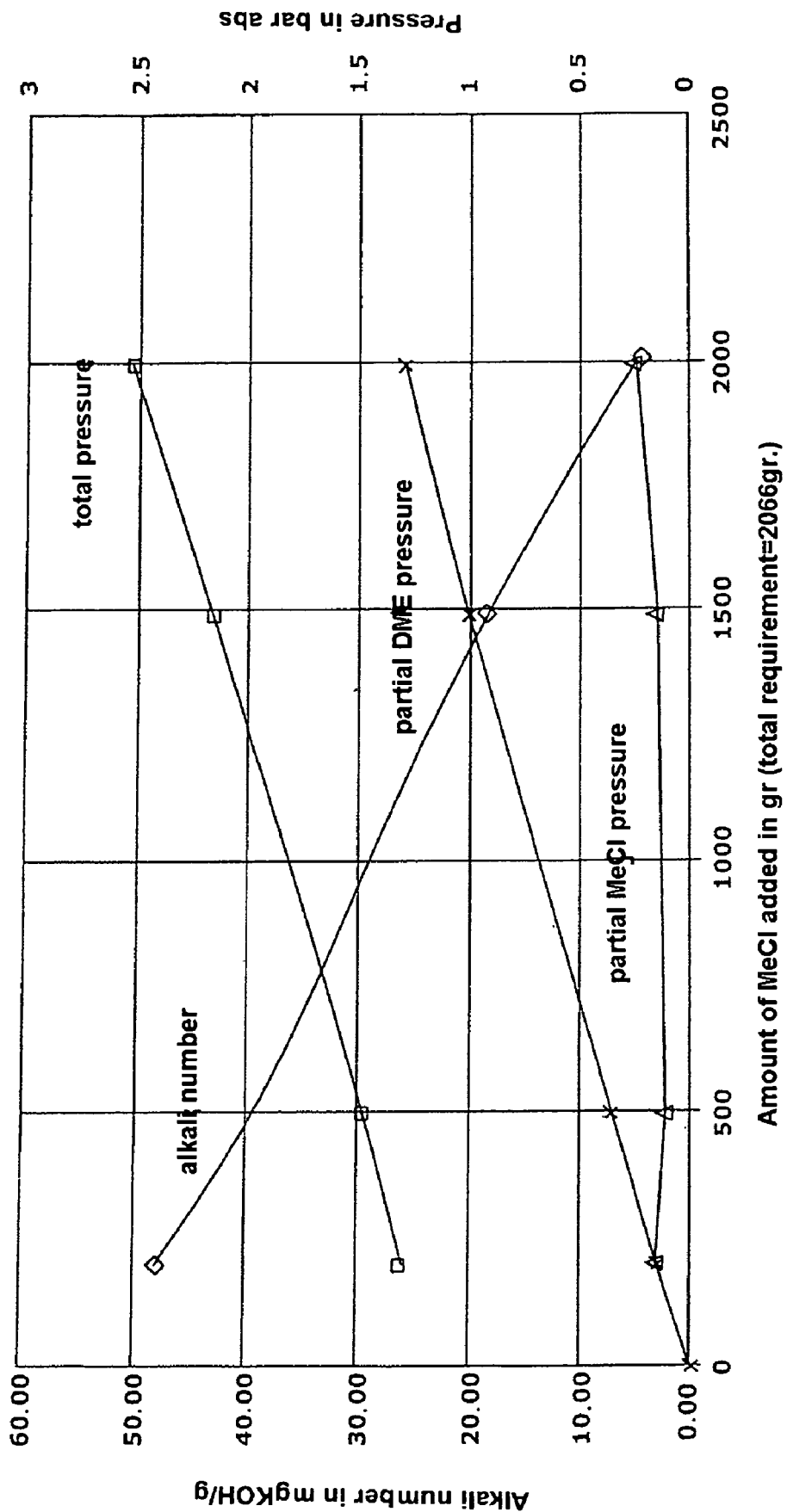
FIG. 2 depicts a plot of alkali number, total pressure and partial MeCl/DME pressures in methylation.

FIGS. 2 and 3 show the effectiveness of the reaction of liquid polyether alkoxide with gaseous methyl chloride in the loop reactor with ejector. Methyl chloride reacts to completion in this system so rapidly that the holdup or partial pressure of methyl chloride in the gas phase is extremely low (FIG. 2) and, on interruption of the methyl chloride dosage, the methyl chloride holdup reacts to completion very rapidly (within less than five minutes) in comparison to a stirred reactor (FIG. 3).

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A process for performing two chemically successive reactions in a loop reactor, comprising
   (reaction I) an optionally catalyzed equilibrium reaction of at least two high-boiling liquid reactants, in which essentially one high boiler is formed as an intermediate and at least one low boiler as a by-product, and
   (reaction II) a substantially diffusion-controlled reaction in which the liquid intermediate is reacted with at least one gaseous reactant to give the end product,
   wherein reactions (I) and (II), optionally after a start phase, are allowed to proceed simultaneously in the same loop reactor, and the loop reactor has a connectable gas-liquid circulation system coupled via an ejector mixing nozzle, in which circulated liquid phase is mixed in the ejector mixing nozzle with newly supplied gaseous reactant of reaction (II) (6) and/or gaseous reactant of reaction (II) aspirated by means of the ejector from the reactor via a connectable condenser (5), and fed to the reactor by a liquid jet ejector (2) for the reaction, the low-boiling by-product(s) of reaction (I) and also any low-boiling solvent being condensed and discharged in the condenser continuously over the duration of the process.

2. The process as claimed in claim 1, which is carried out batchwise.

3. The process as claimed in claim 1, which is carried out continuously.

4. The process as claimed in claim 1, wherein, in a start phase, the high-boiling liquid reactants and optionally one or more catalysts are initially charged, the high-boiling liquid reactants optionally being present in a low-boiling solvent, and reaction (I) is carried out with condensation and discharge of the volatile by-product(s) and any solvent, either in a closed condensation gas circuit or by aspirating the inert gases by means of a vacuum unit via a condenser, until the distillation parameters predefined according to the process and plant technology have been attained.

5. The process as claimed in claim 1, wherein the high-boiling liquid reactants and optionally one or more catalysts are initially charged, and the high-boiling liquid reactants may be present in a low-boiling solvent, and reactions (I) and (II) are carried out substantially without a start phase.

6. The process as claimed in claim 1, in which offgas incineration is additionally carried out and the by-product from reaction (I) is used as carrier fuel.

7. The process as claimed in claim 1 for etherifying high-boiling, liquid alkyl- or alkenyl-started polyether alcohols of the general formula (1)

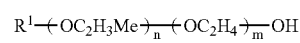

$$R^1-(OC_2H_3Me)_n-(OC_2H_4)_m-OH$$

where
R$^1$ is an alkyl- or alkenyl radical having 1 to 5 carbon atoms,
Me is a methyl radical,
n and m are each an integer in the range from 0 to 90 and the sum of n+m is in the range from 5 to 90,
in a loop reactor, comprising,
as reaction (I) a deprotonation of the polyether alcohol, with a high-boiling, liquid alkali metal methylate, ethoxide or propoxide, optionally in the presence of a low-boiling solvent to form substantially a high-boiling alkali metal polyether alkoxide intermediate and at least one low-boiling alcohol as a by-product and,
as reaction (II), an ether coupling in which the liquid alkali metal polyether alkoxide intermediate is reacted with gaseous alkyl halide to give the end product,
wherein reactions (I) and (II), optionally after a start phase, are allowed to proceed simultaneously and the loop reactor has a gas-liquid circulation system coupled via an ejector mixing nozzle, in which circulated liquid phase is mixed in the ejector mixing nozzle with newly supplied gaseous alkyl halide of reaction (II) (6) and/or gaseous alkyl halide of reaction (II) aspirated by means of the ejector from the reactor via a condenser (5), and fed to the reactor by a liquid jet ejector (2) for the reaction, the low-boiling alcohol(s) of reaction (I) and also any low-boiling solvent being condensed and discharged in the condenser continuously over the duration of the process.

8. The process as claimed in claim 7, wherein a start phase is provided in which the high-boiling liquid polyether alcohol is initially charged, alkali metal methylate, ethoxide or propoxide, optionally dissolved in low-boiling solvent, is added, and reaction (I) is carried out with condensation and discharge of the volatile alcohol(s) and any solvent, either in a closed condensation gas circuit or by aspirating the inert gases by means of a vacuum unit via a condenser, until the distillation parameters predefined according to the process and plant technology have been attained.

9. The process as claimed in claim 7, wherein an upper temperature limit of 130° C. is not exceeded.

10. The process as claimed in claim 7, wherein the reaction is carried out down to a residual alkali number of less than 0.1 mg KOH/g.

11. The process of claim 8, wherein the low-boiling solvent is selected from the group consisting of especially methanol, ethanol, propanol and mixtures thereof.

* * * * *